(12) United States Patent
Alsac et al.

(10) Patent No.: US 10,548,623 B2
(45) Date of Patent: Feb. 4, 2020

(54) CUTTING DEVICE FOR ENDOVASCULAR SURGERY

(71) Applicant: ASSISTANCE PUBLIQUE—HOPITAUX DE PARIS (AP-HP), Paris (FR)

(72) Inventors: Jean-Marc Alsac, Paris (FR); Edouard Dufetelle, Paris (FR)

(73) Assignee: Assistance Publique-Hopitaux de Paris, Paris (FR)

( * ) Notice: Subject to any disclaimer, the term of this patent is extended or adjusted under 35 U.S.C. 154(b) by 249 days.

(21) Appl. No.: 14/414,194

(22) PCT Filed: Jul. 12, 2013

(86) PCT No.: PCT/EP2013/064842
§ 371 (c)(1),
(2) Date: Jan. 12, 2015

(87) PCT Pub. No.: WO2014/009554
PCT Pub. Date: Jan. 16, 2014

(65) Prior Publication Data
US 2015/0148828 A1    May 28, 2015

(30) Foreign Application Priority Data
Jul. 12, 2012  (FR) ..................... 12 56751

(51) Int. Cl.
*A61B 17/3201* (2006.01)
*A61B 17/32* (2006.01)
(Continued)

(52) U.S. Cl.
CPC .. *A61B 17/320016* (2013.01); *A61B 17/3201* (2013.01); *A61B 2017/00778* (2013.01);
(Continued)

(58) Field of Classification Search
CPC .. A61B 2017/32004; A61B 2017/2902; A61B 2017/2908; A61B 2017/22039;
(Continued)

(56) References Cited

U.S. PATENT DOCUMENTS 5,300,087 A * 4/1994 Knoepfler ............. A61B 17/29
604/33
5,762,070 A * 6/1998 Nagamatsu ............ A61B 10/06
600/564
(Continued)

FOREIGN PATENT DOCUMENTS

JP          2002119514 A     4/2002

*Primary Examiner* — Katherine H Schwiker
(74) *Attorney, Agent, or Firm* — Thomas | Horstemeyer, LLP

(57) ABSTRACT

The invention relates to an endovascular cutting device for carrying out surgical or medical operations. According to the invention, such a device includes two cutting blades, a means for remotely actuating the two cutting blades, and at least two flexible guide rods, said cutting blades being slidably mounted onto said guide rods, and said remote actuation means including a flexible transmission means, wherein a channel, through which the flexible guide rods (50) are to be inserted, extends through said cutting blades (11, 12, 101, 102) over the entire outer length thereof.

15 Claims, 7 Drawing Sheets

(51) Int. Cl.
*A61B 17/22* (2006.01)
*A61B 17/00* (2006.01)

(52) U.S. Cl.
CPC ............... *A61B 2017/22039* (2013.01); *A61B 2017/22095* (2013.01)

(58) Field of Classification Search
CPC .. A61B 2017/22097; A61B 17/320016; A61B 17/32; A61B 17/3201; A61B 17/29; A61B 17/295; A61B 17/3205; A61B 17/3207; A61B 17/320725; A61B 17/320783; A61B 17/22031; A61B 10/06; A61B 18/1445; A61B 17/28; A61B 17/285; A61B 17/2812; A61B 17/2816; A61B 17/282; A61B 2017/00778; A61B 2017/22095; A61B 2017/22094; A61B 2017/22038; A61B 2017/22041; A61B 2017/2926; A61B 2017/2825; A61B 2017/2829; A61B 2017/00292; A61B 2018/1452; A61B 2018/1457; A61B 2018/146; A61B 2018/00345; A61B 2018/00404; A61B 2018/00351
See application file for complete search history.

(56) References Cited

U.S. PATENT DOCUMENTS

| | | | | |
|---|---|---|---|---|
| 5,916,193 | A  * | 6/1999 | Stevens | A61M 1/3659 604/28 |
| 8,083,664 | B2 * | 12/2011 | Davis | A61B 17/0218 600/37 |
| 2010/0198244 | A1 * | 8/2010 | Spivey | A61B 17/320016 606/174 |
| 2011/0118769 | A1 | 5/2011 | Bliss et al. | |

* cited by examiner

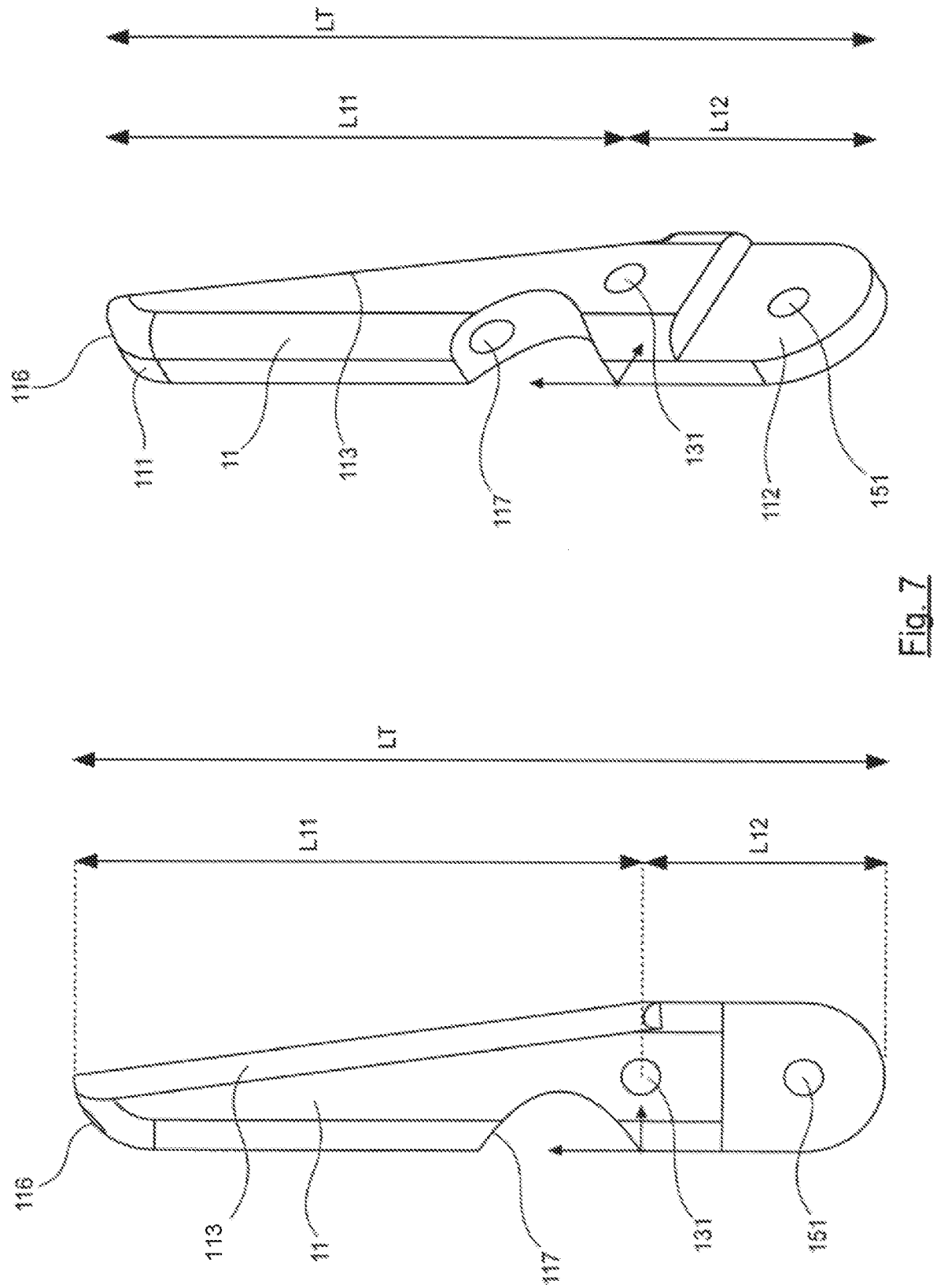

CUTTING DEVICE FOR ENDOVASCULAR SURGERY

CROSS-REFERENCE TO RELATED APPLICATION

This application is the 35 U.S.C. § 371 national stage of PCT Application No. PCT/EP2013/064842, filed Jul. 12, 2013, which is herein incorporated by reference in its entirety and which also claims priority to, and the benefit of, French Patent Application No. 1256751, filed Jul. 12, 2012, which is herein incorporated by reference in its entirety.

1. DOMAIN OF THE INVENTION

The invention relates to medical devices for making surgical or medical operations. More specifically, the invention relates to a cutting device for endovascular surgery operations, particularly for surgery of acute or chronic dissections of the aorta.

2. PRIOR ART

Dissection of the thorax-abdominal aorta is a serious pathology, leading to a fatal prognostic of patients in the short and long term. Risk factors of this type of cardiovascular accident are particularly high blood pressure or congenital pathologies such as Marfan's disease that affects the elastic fibres that form part of the wall of the aorta. The incidence of this pathology is about 1% but the mortality rate of patients is 50% within the first 48 hours (Midulla et al., *Journal of Thoracic and Cardiovascular Surgery* (2011) 66-72). One of the explanations of the low incidence of this pathology is related to the fact that dissection symptoms are not very specific and are frequently confused with symptoms indicating a myocardial infarction. Furthermore, there is not necessarily any thorax pain. The diagnosis of the aorta dissection is then delayed. The only way to confirm the practitioner's suspicions is to perform imagery techniques such as magnetic resonance imagery, thorax scan or transoesophagian ultrasound scan.

Anatomically, an aortic dissection is characterised by the irruption of blood inside the aortic wall. More precisely, the first phase is tearing at the intima, the inner sheet of the aortic wall. Blood flowing from the heart floods into the tear and as a result of the pressure that it applies on the tissue, enters between the superposed sheets forming the aorta wall, also referred to as media. In doing so, it forms a second channel inside which blood accumulates. A second tear sometimes occurs at a distance from the first tear, through which blood exits and rejoins the true channel. The main and natural channel will be referred to as the true channel in the following description, while the channel created by the dissection will be referred to as the false channel.

The DeBakey's classification makes a distinction between three dissection types as a function of their anatomic origin:
  type 1: the dissection begins on the ascending aorta, extends on the aortic arch and ends on the descending aorta;
  type 2: the dissection begins and ends on the ascending aorta, and
  type 3: the dissection begins, extends and ends on the descending aorta.

The main complication of the aortic dissection is the result of the fact that the blood pressure in the false channel is too high, consequently it compresses the blood circulation in the true channel. This pressure gradient between the two channels is related to the fact that the resistance opposing the blood flow in the false channel is too high. Consequently, blood circulates badly in the portion of the dissected aorta and the result is poor perfusion of the arteries irrigating the lower organs and limbs. If compression of the true channel by the false channel is not quickly released, the organs for which perfusion depends on the aorta will quickly experience malfunctions, sometimes irreversible. The heart tires quickly, trying to direct blood that it receives to the aorta, although the orifice in the artery is compressed.

Therefore, it is urgent to restore a balance between pressures between the two channels and consequently blood circulation in the vital organs. One urgent treatment consists of closing the breach by inserting an endoprosthesis as far as the dissection location, through the femoral artery, under radioscopy monitoring. The endoprostheses used are covered by a synthetic tissue to block access of blood to the false channel. Although this is efficient, it is sometimes impossible to use endoprosthesis due to difficult anatomic conditions, or insufficient considering the fact that there are other reentry orifices.

Another option consists of tearing the flap separating the channels. This technique is called fenestration and is shown in FIG. 1. This is done by inserting two guide rods or guides 50 into the patient's aorta through the femoral artery and moving them upwards as far as the location of the dissection under radioscopic monitoring. One of the guides 50 goes through the true channel 1 of the aorta A while the second guide 50 is inserted in the false channel 2 through a tear 5. An introducer 3 about 3 mm diameter comprising a central orifice 31 is then introduced on the guides. Once the surgeon feels that the introducer stops in contact with the flap 4, he applies pressure to tear it backwards. Once the flap has been torn, the pressure between the true and the false channels becomes balanced, the true channel 1 is decompressed and the visceral arteries are then quickly revascularised. The fenestration technique is very efficient in the case of an emergency. However, the practitioner does not have very good control over it because he has to work "blind" despite radioscopic monitoring.

However, dangers related to aortic dissection are not limited to the acute phase. In 60% of cases, dissection progresses towards an extensive dissecting aneurysm, namely the formation of an intraparietal pouch full of blood, at the dissection. These aneurysms have a serious risk of rupture due to the high blood pressure inside them, and to degeneration of the remaining wall of the aorta. An aneurysm with a size of 65 mm is an indication of the need for a preventive operation to prevent a sudden rupture that would be fatal. Furthermore, it is rare that the dissection diagnosis is made in the acute phase. The flap separating the true channel from the false channel is then completely stiffened over time, due to the development of a fibrous scar tissue.

Constraints on the treatment of aortic dissections in the chronic phase are different from the treatment of aortic dissections in the acute phase. Thus, the use of endoprostheses fitted with visceral branches is a choice that can only rarely be put into practice in this type of chronic aneurysmal dissection. The use of endoprostheses with visceral branches can only be envisaged in the true aortic channel because very often rigidification of the flap makes catheterisation of the visceral arteries impossible. Therefore, this solution is completely unacceptable.

An alternative has recently been disclosed; this is to place a "flow diverter" type stent at the dissecting aneurysms. This device is currently used to treat intracranial aneurysms (Pierot, *Journal of Neuroradiology* (2011), 38, 40-46). Similarly, this type of endoprosthesis can only be placed in the true channel, since the false channel remains permeable.

The fenestration technique using an introducer as described above is also unacceptable; although it can give good results with a flexible flap during the first days after the dissection, tearing becomes impossible and even dangerous with a flap that has become rigid over time. The surgeon would then be obliged to apply pressure on the flap that could break suddenly and weaken the aorta or even cause its rupture, which would be fatal for the patient.

Since these treatments are unacceptable, all that remains is open surgery, in other words the patient is opened up at the thorax-abdomen level so that the surgeon can operate on the aorta directly. However, open surgery is very difficult, both for the patient and for the medical team. There are many complications related to such an operation (death, paraplegia, terminal renal insufficiency, etc.), and post-operation recovery is long and difficult for the patient. It is also very expensive for the health system. These risks are particularly high when patients usually have subjacent pathologies such as high blood pressure, and a poor general condition. Furthermore, it frequently happens that these patients cannot receive this type of surgery because the dangers are worse than the benefits.

Therefore, a device is necessary that can extend the indications of endovascular surgery acts, limiting the invasive nature of operations and allowing the practitioner to perform operations for aortic dissecting aneurysms regardless of the rigidification stage of the flap.

3. PURPOSES OF THE INVENTION

The purpose of the invention is particularly to overcome these disadvantages according to prior art.

More specifically, one purpose of the invention is to provide a surgical device in at least one embodiment, capable of cutting the vascular wall or "flap" of a dissection, regardless of its stage of rigidity.

Another purpose of at least one embodiment of the invention is to use a surgical device limiting the invasive nature of the surgical act for the patient.

Another purpose of at least one embodiment of the invention is to disclose an endovascular surgical device that the practitioner can use to improve the reliability and precision of his operation.

4. PRESENTATION OF THE INVENTION

These purposes and others that will become clear later, are achieved by means of an endovascular cutting device for the use of surgical or medical operations.

According to the invention, such a device comprises two cutting blades, means of remote actuation of two cutting blades and at least two flexible guide rods, said cutting blades being installed free to slide on said guide rods and said remote actuation means including flexible transmission means.

Thus, the invention is based on an innovative method and discloses an endovascular surgical device so that the practitioner can cut a piece of vascular wall commonly referred to as a flap, rather than tear it off in an approximate and uncontrolled gesture. It is important to specify that this cutting gesture is a clean action fully controlled by the practitioner. It does not involve tearing or ripping the flap using any type of instrument. The practitioner uses the device according to the invention to make a perfect cut of the flap, and he personally controls the force applied on the flap by the blades and also the speed at which the gesture is performed. Therefore, the practitioner's gesture is much safer and more precise, which is much more comfortable for the surgeon and much safer for the patient. Unlike the use of the introducer in the conventional backward fenestration technique, the device according to the invention can be used to operate on aortic dissections in the acute phase and also in the chronic phase when the flap has already begun to become rigid.

The flexibility or suppleness of the transmission means are such that the sliding device can be inserted into the arterial vascular system on two guide rods and can follow meanders without any risk of injury or perforation of a vessel. Although it is technically difficult to have remote control over the operation of the cutting blades, the movement of blades on the guide rods firstly directs the cutting blades reliably and precisely until they come into contact with the flap to be cut and secondly stabilises the cutting blades so that their remote operation can be controlled.

Furthermore, patients may be treated with the device according to the invention regardless of the stage of progress of their pathology. Furthermore, such a device according to the invention is designed to operate on a patient in mini-invasive surgery, which can limit the morbid nature of the operation. It can also enable the use of an aortic endoprosthesis for endovascular treatment of aneurysms of the aorta that have only been possible up to now by much more destructive open surgery Mini-invasive surgery refers to surgical procedures by which the surgeon can reach the internal organs by making an incision of the order of one centimetre long on the patient's skin, using long and thin instruments coupled to an imagery system. Risks and complications related to open surgery are avoided, therefore more patients can benefit from the treatment.

The cutting device is preferably operated manually. However, the device can also be used by radiofrequency or other electrical energies. According to the invention, the device must be perfectly leak-tight along all the transmission means. This characteristic is important because it makes it possible to prevent the ingress of blood into the mechanism of the device and any other malfunctions that might occur.

In one preferred embodiment of the invention, a channel at least partly passes longitudinally through the cutting blades for insertion of the guide rods. Insertion of the guide rods into a channel formed inside the thickness of the blades provides means of guiding the blades more precisely and in a more stable manner along the guide rods. The longer the channel, the better the blades slide on the rods in a more stable manner. Preferably, the channel in which a guide rod is inserted extends over the outer length of each cutting blade. Thus, the practitioner's gesture is better controlled and safer. Therefore, this characteristic contributes to improving the precision of the practitioner's gesture to cut the flap.

On the other hand, a channel that only extends over a portion of the length of the cutting blades will allow faster and more flexible sliding.

In another preferred embodiment of the invention, each cutting blade has at least one ring through which guide rods can be inserted. In this embodiment, at least one ring is fixed onto each blade, the guide rods moving in the orifice of the ring. This embodiment allows fast and flexible sliding of the device according to the invention along the guide rods.

In one advantageous embodiment, the remote actuation means also include a control element. This element allows the practitioner to manipulate the cutting device himself and to actuate the cutting blades at the appropriate moment, while enabling him to adjust the movement and actuation speed of the blades.

Preferably, the flexible transmission means include a flexible actuation cable mounted free to slide in a catheter, said actuation cable being connected at its proximal part to a control element and at its distal part to the two cutting blades. In this embodiment, the relative movement of the actuation cable is limited in comparison with the movement of the catheter. Advantageously, the control element includes a pair of branches, one of the branches being rigidly fixed to the catheter and the other branch being hinged to the actuation element, the branches being connected and hinged to each other. This characteristic allows the practitioner, simply by manipulating the pair of branches, to slide the actuation cable inside the catheter, this relative movement of the cable from the catheter controlling opening and closing of the cutting blades. Also more preferably, the control element comprises a pair of branches chosen from among branches with clamps or branches with rings.

Preferably, the cutting blades are hinged on the actuation cable.

Advantageously, the cutting blades have an opening angle $\alpha$ between 0 and 60°. The angle $\alpha$ is zero when the blades are in the closed position and the device is moved in the vessels as far as the location of the operation and the angle $\alpha$ is not zero in the open position. This characteristic makes it possible to manipulate the device according to the invention, and in particular to actuate the cutting blades within the vessel, without damaging the inner vascular walls and creating unnecessary lesions. This parameter is particularly important if the inner walls are already weakened.

In one preferred embodiment, the two cutting blades rotate about their longitudinal axis at an angle $\beta$ between 0 and 360°. This characteristic provides an additional degree of manipulation of the two cutting blades, so that lesions can more easily be accessed.

Preferably, the guide rods are made of polytetrafluoroethylene (PTFE) or nitinol. This material has the advantage that it is biocompatible; it can be inserted into the human body without any harmfulness. Furthermore, this material is flexible and strong so that it can easily be manipulated through meanders of the vascular system without creating any risk of rupture. Finally, PTFE makes it possible to manufacture very smooth guide rods which makes sliding of the cutting blades very much easier. The fact that the guide rods are smooth makes it easy for the blades to not get caught along the rods, limiting friction between the material of the guide rods and the material from which the cutting blades are made. Thus, the cutting device is routed by a safe and perfectly controlled gesture of the practitioner until it reaches the location of the operation. In one even more preferred embodiment, the materials from which the device is made are chosen from among steel and nitinol. These materials have the advantage of being biocompatible, resistant to corrosion and sterilisation.

Another aspect of the invention also relates to an aortic dissection fenestration method, the purpose of which is to cut the vascular wall separating the true channel from the false channel, and includes the following steps:
  insert two guide rods in the patient's vascular channel;
  position one of the guide rods in the true channel and position the other guide rod in the false channel;
  insert each guide rod in each of the two cutting blades outside the patient;
  insert the endovascular cutting device according to the invention through the patient's vascular channel;
  route the device according to the invention inside the vascular channels until it comes into contact with the vascular wall separating the true channel and the false channel;
  actuate the cutting blades making use of the remote actuation means and actively cut the required portion of the vascular wall;
  remove the cutting device and the guide rods from the patient's body.

Thus, the fenestration method according to the invention can be used to operate on aortic dissections in the acute phase and in the chronic phase.

5. LIST OF FIGURES

Other characteristics and advantages of the invention will become clear after reading the following description of a preferred embodiment, given as an illustrative and non-limitative example, and the appended drawings in which:

FIG. 7 shows a view of a cutting blade.

6. DESCRIPTION OF ONE EMBODIMENT OF THE INVENTION

The general principle of the invention is based on the use of an endovascular cutting device comprising two cutting blades, capable of cutting any vascular wall regardless of its state of rigidity, mounted free to slide on two guide rods that act as rails to bring the cutting blades into contact with the wall to be cut. The remote control means allow the use of mini-invasive surgery while the supple and flexible transmission means make it possible to direct the device without any risk of injury or perforating the vascular wall.

Figure 1:
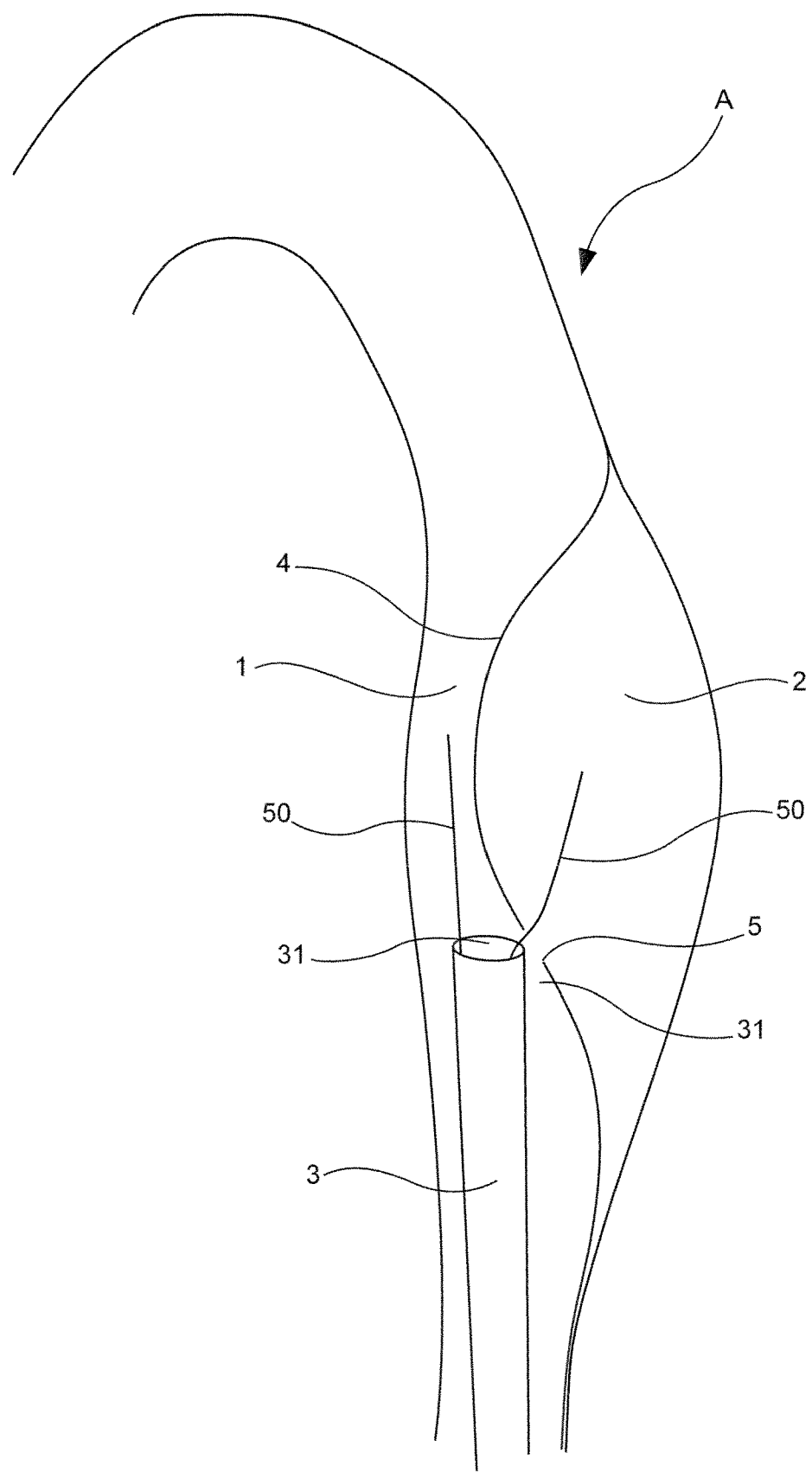
FIG. 1 shows the conventional fenestration technique on a dissection in the acute phase.
Figure 2:
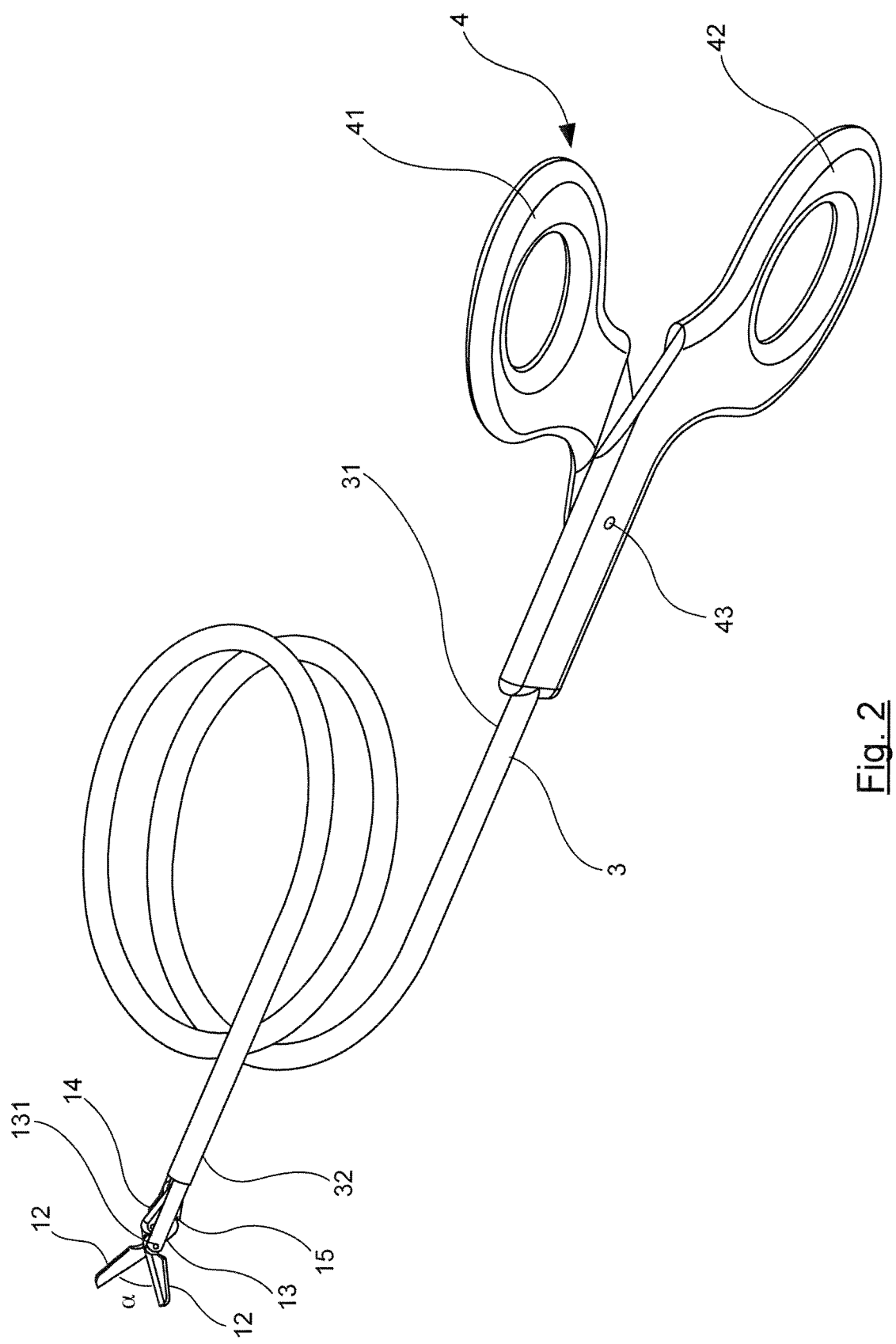
FIG. 2 shows an overview of one embodiment of the device according to the invention, in the open position.

We will now present an overview of one embodiment of the device according to the invention with reference to FIG. 2, adapted to make an aortic dissection in its acute phase, and in the dissecting aneurysm phase.

As shown, the device according to the invention comprises a control element 4 comprising a pair of branches with rings 41, 42, the branches being crossed and hinged to each other through a hinge pin 43. The control element 4 is connected to a catheter 3 at the proximal part of the catheter 31.

Such a catheter will preferably have a diameter of between 5 and 7 mm. There is an actuation cable housed inside the catheter not shown in the figure for reasons of clarity. The diameter of the actuation cable will preferably be between 4 and 6 mm so that it can slide inside the catheter 3. The catheter and actuation cable assembly are between 40 mm and 100 mm long. The length of the catheter and the actuation cable will depend on the anatomic location of the lesion to be operated on. This parameter will be easily determined by those skilled in the art, making use of their general knowledge. The catheter and the actuation cable contained in it are both flexible and supple. This characteristic makes it easy to navigate within the vascular system without any risk of damaging it.

The catheter 3 is connected to the two cutting blades 11, 12 at its distal part 32 through an attachment element 13. As shown in FIG. 2, the cutting blades 11, 12 are at a distance from each other and form an angle α. When the cutting blades are separated from each other and their angle α is not zero, they are in the open position. When the angle α is zero, the cutting blades are in the closed position. The blades are in the closed position when they are inserted into the body. Preferably, each of the cutting blades has a rounded proximal end, to avoid injuring the vascular walls during their operation or during their routing. The cutting blades are crossed and hinged together at a hinge pin 131, this hinge pin 131 being used to articulate them with the attachment part 13. Each cutting blade 11, 12 is hinged at its distal part by a connecting rod 15, 14. The guide rods 50 are not shown on this view. The cutting blades, the connecting rods and the attachment part are made of a biocompatible metallic material such as steel or nitinol. It should be noted that on this view, this device is shown wound on itself to illustrate the flexibility of the actuation cable and the catheter.

A) Example of a First Embodiment

Figure 3:
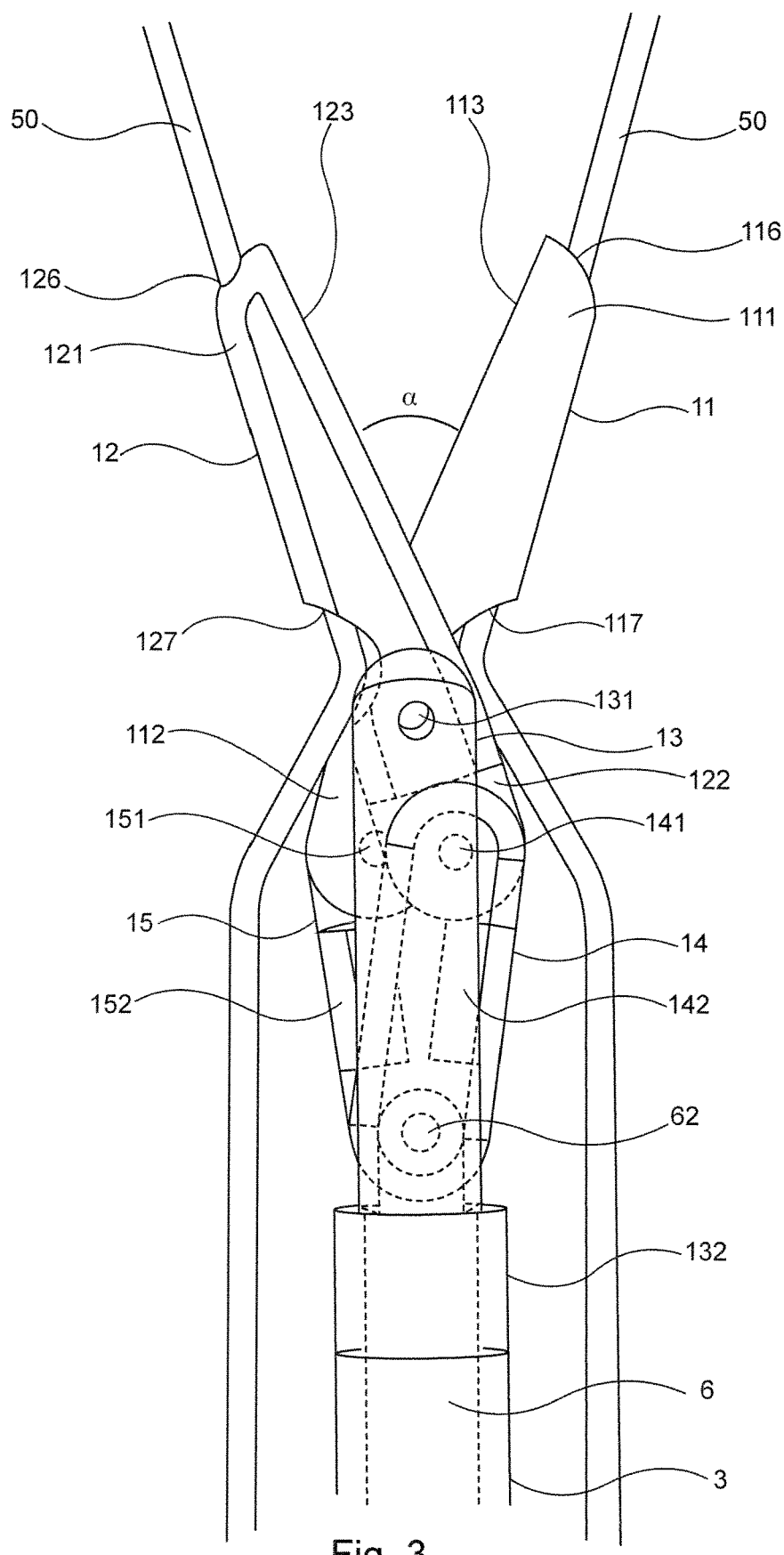
FIG. 3 shows a view of the cutting blades according to FIG. 2 in the open position.
Figure 4:
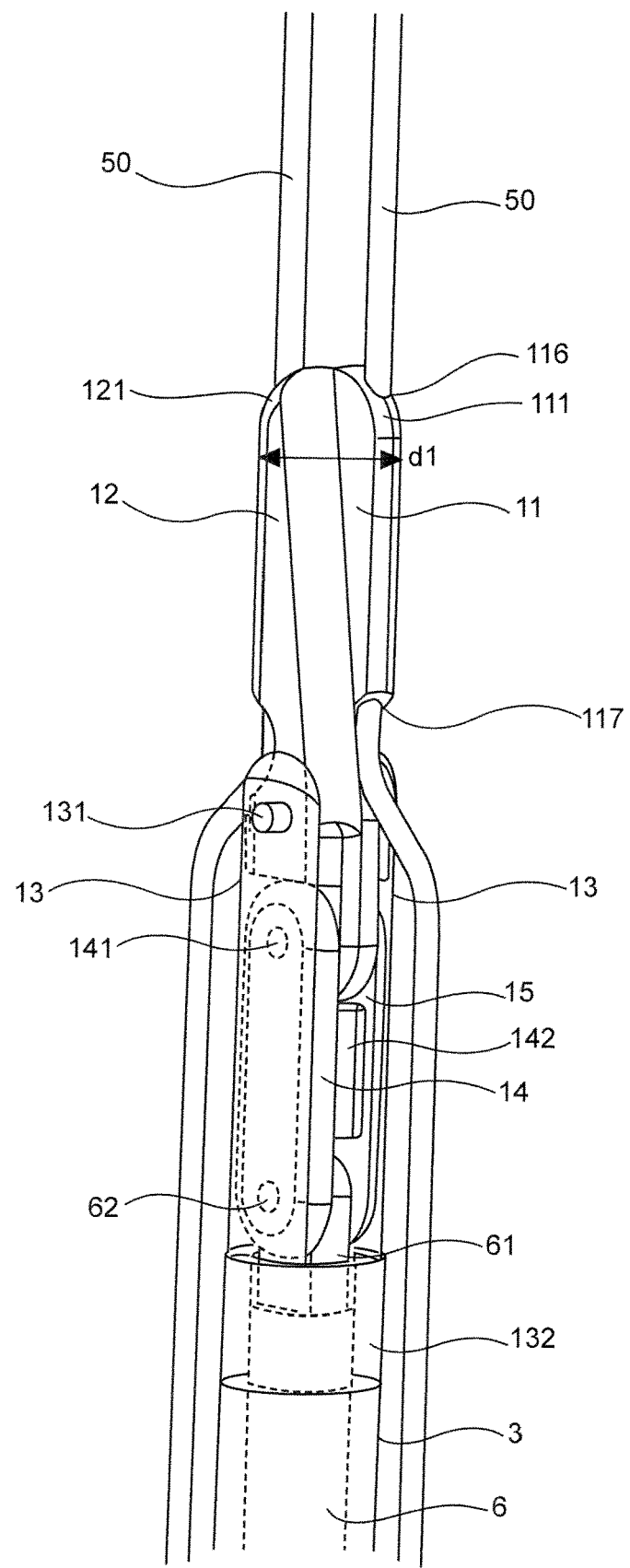
FIG. 4 shows a view of the cutting blades according to FIG. 2 in the closed position.

FIGS. 3 and 4 show a detailed view of the cutting blades of a first embodiment according to the invention, in the open and closed positions respectively. The hidden parts are shown in dashed lines. Each of the cutting blades 11, 12 has a rounded distal end 111, 121, and a proximal end 112, 122. This rounded form means that the cutting blades can be inserted in the closed position without creating any lesions in the inside wall of the vessels inside which the device passes. It also makes it possible to actuate the cutting blades safely within a vessel. This characteristic is particularly important when operating on a patient who already has intravascular lesions. Each blade has a cutting edge 113, 123 used to cut the vascular wall, even when a fibrous scar tissue has begun to develop. Blades are hinged to each other by a hinge pin 131, that also holds them to the attachment part 13. Each blade 11, 12 is hinged at its proximal part to a connecting rod 14, 15, the blade 11 also being connected to the connecting rod 15 through a hinge pin 151 and the blade 12 being connected to the blade 14 through a hinge pin 141. In order to prevent movement bringing them into contact with each other, and to hold the blades 11, 12 in line with each other in the closed position, each connecting rod 14, 15 has a stop 142, 152. The connecting rods 14, 15 are hinged together through a hinge pin 62. This hinge pin also allows them to cooperate with the actuation cable 6 at its distal part 61. The attachment part 13 has a ring in its proximal part 132, into which the catheter 3 can be force fitted.

According to the invention, the blades are mounted free to slide along two guide rods 50. These flexible guide rods 50 are made of nitinol or PTFE and have a circular section with a diameter of 0.035 inch, which is about 1 mm. For example, the commercial references Lunderquist-Ring Torque Wire Guides, Cook Inc. or Radifocus® Guide Wire, Terumo are suitable as guide rods for implementation of the invention. The guide rods are inserted outside the patient, inside the orifices 117, 127 of channels each passing through the cutting blades 11, 12 and exit through the orifices 116, 126. In this embodiment, the channels extend approximately along the longitudinal axis of each blade 11, 12 over at least part of the length of the blades. It should be noted that the cutting blades have an opening angle α, measured between the longitudinal axes of each blade 11, 12, that cannot exceed 60°. This opening angle is limited so as to not open the cutting blades excessively and risk injuring the inner wall of the vessels. The cutting blades can also be free to move at an angle β equal to 360° about their longitudinal axis (not shown on the figures).

Figure 5:
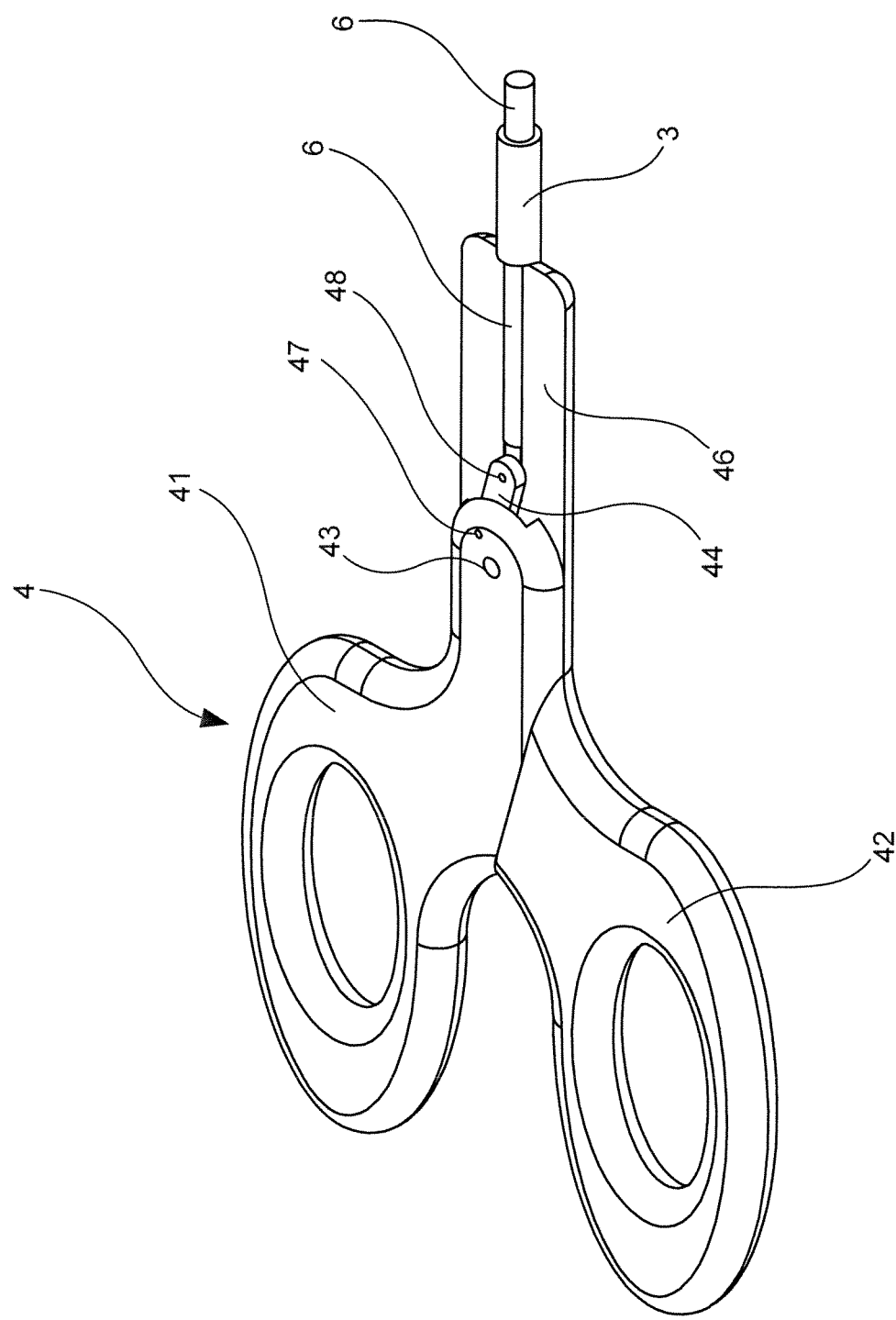
FIG. 5 shows a view of the control handle of a device according to the invention.

FIG. 5 shows a schematic view of the control element 4 of a device according to the invention. This control element 4 comprises a pair of branches with rings 41, 42. The surgeon uses the rings to grip the device. The branches 41, 42 are hinged to each other by a hinge pin 43. This hinge pin is also used to connect each of the branches to a plane part 46. Therefore, the branch 42 is connected to the plane part through the hinge pin 43, this plane part being connected to the catheter 3 by gluing, thermoforming or welding. The branch 42 is hinged to the actuation cable 6 through a connecting rod 44. More specifically, the branch 42 is hinged to the connecting rod 44 through a hinge pin 47 while the connecting rod 44 is also hinged with the actuation cable 6 through a hinge pin 48. Each branch with rings also comprises a stop as is conventionally the case with a pair of scissors.

Thus, when the surgeon separates the rings on each of the branches 41, 42 from each other, the cable 6 is pulled towards the surgeon, inside the catheter 3 that remains fixed. The relative movement of the cable in the catheter provides remote control of the cutting blades. More precisely, the part 61 pulls the connecting rods 14,15 that come into contact with the ring 132 on the attachment part. The ring prevents the connecting rods from moving backwards which causes the distal parts 142, 152 of each of the connecting rods 14, 15 to move away from each other. This movement also causes the separation of the cutting blades 11, 12 that are in the open position as shown in FIG. 3. Similarly, the movement of the branches with rings towards each other causes the alignment of connecting rods 14, 15 and alignment of cutting blades 11, 12 with the longitudinal axis of the cable 6 and the catheter 3, as shown in FIG. 4. Thus, the surgeon can make a simple opening movement of the scissors to make a simple, fast and efficient cut of the flap separating the true channel from the false channel. The edge 123, 113 of each cutting blade 11, 12 is sufficiently sharp to perform operations on the pieces of the vascular wall that have become rigid through the development of scar tissue. Furthermore, cutting blades 11, 12 are stabilised during their operation and actuation due to the presence of the guide rods.

Figure 6:
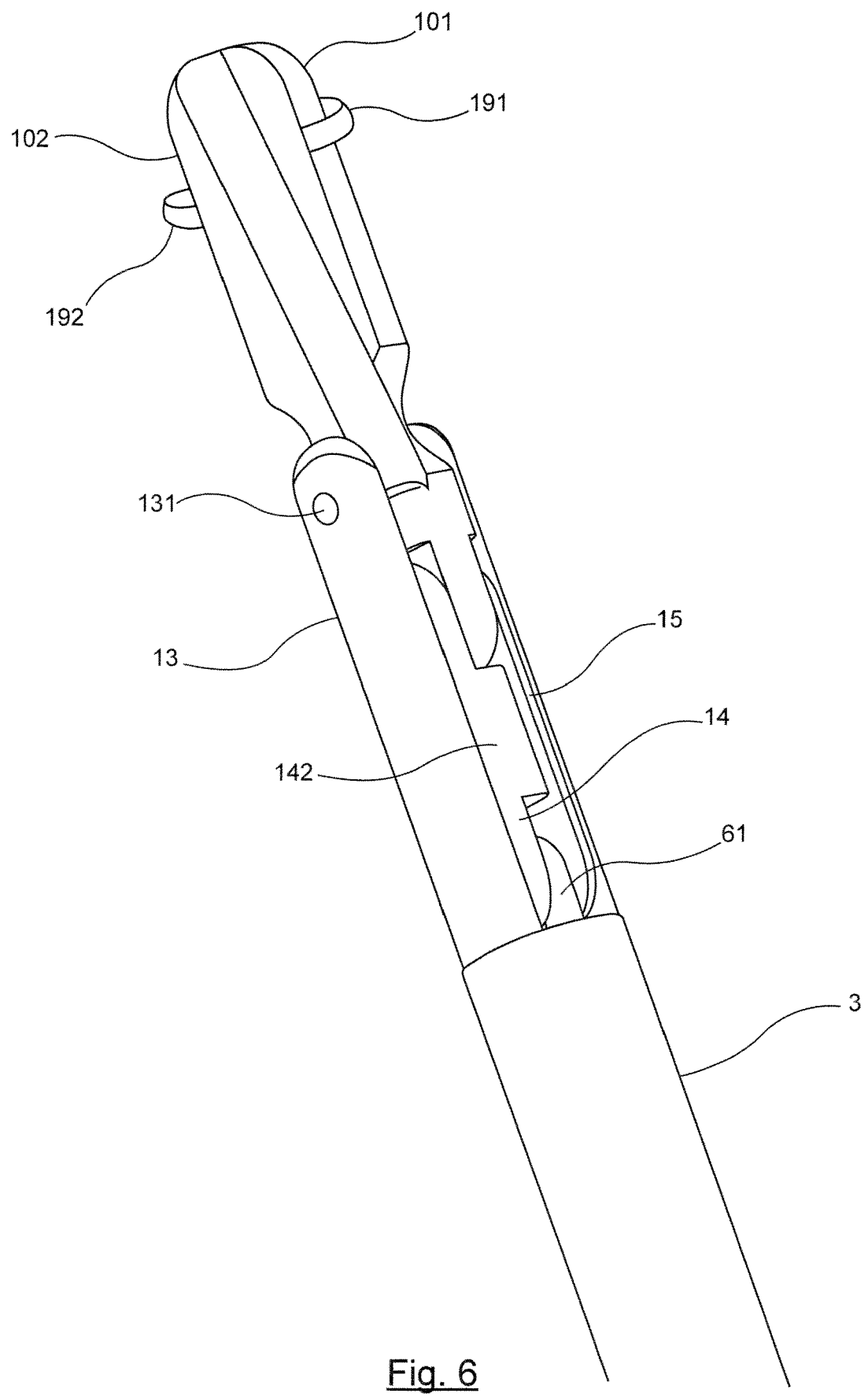
FIG. 6 shows a variant of a device according to the invention.

The dimensions of the different elements making up the device according to the invention are directly dependent on their anatomic destination and the characteristics of the vessels into which they are inserted. The dimensions of the cutting blades are shown in FIG. 7. For example, the dimensions of the device to cut the flap of an aortic dissection could be as follows:

catheter diameter: 5 to 7 mm
diameter of guide rods: 1 mm
diameter of the transmission cable: 5 mm
diameter d1 of the cutting blades: 5 mm
length L1 of the cutting blades: 3 cm
length L11 of the blades: 1 cm
length L12 of the blades: 2 cm
length of the connecting rods L2 14,15: 2 cm
length L3 of the attachment part 13:
total length L4: maximum 5 cm
length of the catheter 3: 40 to 100 cm b) Example of a Second Embodiment According to this second embodiment shown in FIG. 6, the cutting blades 101, 102 are solid and slide along the guide rods 500 by means of the rings 191, 192. The thickness of the rings is about 2 mm, their outer diameter is approximately 2 mm.

Operation and articulation of the cutting blades with the connecting rods 14, 15, the attachment part 13, the cable 6, the catheter 3 and the control element 4 are identical in all respects with the example described in section 5*a*). The part dimensions are identical to the first embodiment.

7. CONCLUSION

The device according to the invention can be used to operate on a patient suffering from an aortic dissection or an aortic dissecting aneurysm, in an only slightly invasive manner. Therefore, this device can be used to apply the fenestration technique, hereto reserved for opening flexible dissections flaps in the acute phase, for the treatment of aneurysms occurring on the chronic dissection. This progress is possible due to the cooperation of two active cutting blades so that the flaps can be cut regardless of their stage of rigidity, remotely controlled by a control element manipulated by the surgeon and connected to the cutting blades through an actuation cable. The flexibility of the catheter and the actuation cable are important characteristics of the device because they can be used to insert and route the device according to the invention through the meanders of the vascular system without any risk of injuring the patient. Finally, sliding of the cutting blades along the guide rods makes it possible to remotely bring the blades into contact with the flap to be cut, by positioning it as close as possible to the flap, and stabilising the cutting blades when the surgeon actuates the control element.

Thus, the surgeon has a better control of his gesture, and cutting is more precise. Risks related to tearing of the rigidified flap are eliminated. The fenestration technique can then be applied to all patients regardless of the stage of progress of their pathology. Patients who are ineligible for open surgery due to their poor physical condition can now be taken care of.

The invention claimed is:

1. A cutting device for endovascular surgical or medical operations comprising two cutting blades, a remote actuator of the two cutting blades, and at least two flexible guide rods; the two cutting blades being installed free to slide on the at least two flexible guide rods and the remote actuator including flexible transmission means, wherein the two cutting blades are crossed and hinged together at respective proximal portions of the two cutting blades, wherein a first longitudinal channel is formed in a cutting portion of a first cutting blade of the two cutting blades and passes along a longitudinal axis of the first cutting blade over at least part of an outer length of the first cutting blade opposite to a first cutting edge of the first cutting blade, the first longitudinal channel is configured for insertion of a first flexible guide rod of the at least two flexible guide rods, wherein the first longitudinal channel has (a) a proximal orifice at a proximal end of the cutting portion of the first cutting blade and (b) a distal orifice at a distal end of the cutting portion of the first cutting blade, wherein the first longitudinal channel has a length from the proximal orifice to the distal orifice, wherein the length of the first longitudinal channel is entirely within a wall of the first cutting portion, and wherein a second longitudinal channel is formed in a cutting portion of a second cutting blade of the two cutting blades and passes along a longitudinal axis of the second cutting blade over at least part of an outer length of the second cutting blade opposite to a second cutting edge of the second cutting blade, the second longitudinal channel is configured for insertion of a second flexible guide rod of the at least two flexible guide rods, wherein the second longitudinal channel has (a) a proximal orifice at a proximal end of the cutting portion of the second cutting blade and (b) a distal orifice at a distal end of the cutting portion of the second cutting blade, wherein the second longitudinal channel has a length from the proximal orifice to the distal orifice, wherein the length of the second longitudinal channel is entirely within a wall of the second cutting portion.

2. The cutting device according to claim 1, wherein the remote actuator also includes a control element.

3. The cutting device according to claim 1, wherein the flexible transmission means include a flexible actuation cable mounted free to slide in a catheter, the actuation cable having a proximal part and a distal part, the actuation cable being connected at the proximal part to a control element and at the distal part to the two cutting blades.

4. The cutting device according to claim 3, wherein the control element includes a pair of branches, a first branch of the pair of branches being rigidly fixed to the catheter and a second branch of the pair of branches being hinged to the actuation cable, the first branch and the second branch being connected and hinged to each other.

5. The cutting device according to claim 3, wherein the two cutting blades are hinged on the actuation cable.

6. The cutting device according to claim 1, wherein the two cutting blades have an opening angle ($\alpha$) of less than 60° formed between the first and second cutting edges.

7. The cutting device according to claim 1, wherein the two cutting blades rotate about a longitudinal axis at an angle ($\beta$) between 0 and 360°.

8. The cutting device according to claim 1, wherein the remote actuator is configured to actively cut a portion of a vascular wall while the first and second flexible guide rods remain inserted in the first and second cutting blades, respectively.

9. A method for aortic dissection fenestration, comprising:
providing a cutting device to cut a vascular wall separating a true channel from a false channel, the cutting device comprising two cutting blades, a remote actuator of the two cutting blades, and at least two flexible guide rods; the two cutting blades being installed free to slide on the at least two flexible guide rods and the remote actuator including flexible transmission means,
wherein the two cutting blades are crossed and hinged together at respective proximal portions of the two cutting blades, wherein a first longitudinal channel is formed in a cutting portion of a first cutting blade of the two cutting blades and passes along a longitudinal axis of the first cutting blade over at least part of an outer length of the first cutting blade opposite to a first cutting edge of the first cutting blade, the first longitudinal channel is configured for insertion of a first flexible guide rod of the at least two flexible guide rods, wherein the first longitudinal channel has (a) a proximal orifice at a proximal end of the cutting portion of the first cutting blade and (b) a distal orifice at a distal end of the cutting portion of the first cutting blade, wherein the first longitudinal channel has a length from the proximal orifice to the distal orifice, wherein the length of the first longitudinal channel is entirely within a wall of the first cutting portion, and wherein a second longitudinal channel is formed in a cutting portion of a second cutting blade of the two cutting blades and passes along a longitudinal axis of the second cutting blade over at least part of an outer length of the second cutting blade opposite to a second cutting edge of the second cutting blade, the second longitudinal channel is configured for insertion of a second flexible guide rod of the at least two flexible guide rods, wherein the second longitudinal channel has (a) a proximal orifice at a proximal end of the cutting portion of the second cutting blade and (b) a distal orifice at a distal end of the cutting portion of the second cutting blade, wherein the second longitudinal channel has a length from the proximal orifice to the distal orifice, wherein the length of the second longitudinal channel is entirely within a wall of the second cutting portion;

inserting the first flexible guide rod and the second flexible guide rod in a vascular channel of a body of a patient;

positioning the first flexible guide rod in the true channel and the second flexible guide rod in the false channel;

inserting, outside of the patient, the first flexible guide rod in the first cutting blade and the second flexible guide rod in the second cutting blade;

inserting the cutting device through the vascular channel of the patient;

routing the cutting device inside the vascular channel until it comes into contact with the vascular wall separating the true channel and the false channel;

actuating, using the remote actuator, the two cutting blades to actively cut a portion of the vascular wall, while the first and the second flexible guide rods remain inserted in the first and second cutting blades, respectively; and removing the cutting device and the at least two flexible guide rods from the body of the patient.

10. The method according to claim 9, wherein the remote actuator also includes a control element.

11. The method according to claim 9, wherein the flexible transmission means includes a flexible actuation cable mounted free to slide in a catheter, the actuation cable having a proximal part and a distal part and being connected at the proximal part to a control element and at the distal part to the two cutting blades.

12. The method according to claim 11, wherein the control element includes a pair of branches, a first branch of the pair of branches being rigidly fixed to the catheter and a second branch of the pair of branches being hinged to the actuation cable, the first branch and the second branch being connected and hinged to each other.

13. The method according to claim 11, wherein the two cutting blades are hinged on the actuation cable.

14. The method according to claim 9, wherein an opening angle ($\alpha$) formed between the first and second cutting edges is less than 60°.

15. The method according to claim 9, wherein the two cutting blades rotate about a longitudinal axis.

* * * * *